United States Patent [19]
Reed et al.

[11] Patent Number: 5,710,426
[45] Date of Patent: Jan. 20, 1998

[54] DYNAMIC AND THERMAL MECHANICAL ANALYZER HAVING AN OPTICAL ENCODER WITH DIFFRACTION GRATING AND A LINEAR PERMANENT MAGNET MOTOR

[75] Inventors: Kevin J. Reed, Landenberg, Pa.; Robert L. Danley, Collingswood, N.J.; John R. Reader, Jr., Newark; John W. Schaefer, Wilmington, both of Del.

[73] Assignee: TA Instruments, Inc., New Castle, Del.

[21] Appl. No.: 609,547

[22] Filed: Mar. 1, 1996

[51] Int. Cl.$^6$ .................................................. H01J 3/14
[52] U.S. Cl. .................... 250/237 G; 250/559.4; 250/231.18; 73/800
[58] Field of Search ................. 250/237 R, 237 G, 250/559.4, 231.17, 231.18; 356/374, 334, 305, 328, 32; 73/800, 855, 856; 374/46, 50, 52, 55

[56] References Cited

U.S. PATENT DOCUMENTS

| | | | |
|---|---|---|---|
| 4,019,365 | 4/1977 | Woo | 374/46 |
| 4,033,181 | 7/1977 | Oeser | 73/800 |
| 4,034,602 | 7/1977 | Woo et al. | 73/579 |
| 4,354,764 | 10/1982 | Achermann et al. | 374/56 |
| 4,967,601 | 11/1990 | Teramoto | 73/789 |
| 4,984,469 | 1/1991 | Take et al. | 73/770 |
| 5,154,085 | 10/1992 | Takeda | 73/811 |
| 5,187,987 | 2/1993 | Anderson et al. | 73/852 |
| 5,200,975 | 4/1993 | Kato | 73/789 |
| 5,486,923 | 1/1996 | Mitchell et al. | 250/237 G |
| 5,488,240 | 1/1996 | Hlousek et al. | 250/231.17 |

FOREIGN PATENT DOCUMENTS

| | | |
|---|---|---|
| 02-40545 | 2/1990 | Japan. |
| 02-227647 | 9/1990 | Japan. |
| 03-251752 | 11/1991 | Japan. |
| 04-178537 | 6/1992 | Japan. |

OTHER PUBLICATIONS

Wetton, R.E.; Fisher, J.S.; Pettitt, K.E.; Evans, A. and Duncan, J.C., "Third Generation DMTA Instrumentation," American Laboratory, Jan., 1993, pp. 15–20.

*Primary Examiner*—Que Le
*Attorney, Agent, or Firm*—Crowell & Moring LLP

[57] ABSTRACT

A dynamic and thermal mechanical analyzer incorporating a slide driven vertically in an air bearing guidance system with a large displacement capacity, very low friction and low mass. The position of the slide is measured by digitizing and interpolating two quadrature output signals generated by an optical encoder with very high spatial resolution and a long stroke. A force is applied to the slide using a linear permanent magnet motor with high force, high force linearity and low sensitivity to temperature variations. Position signals derived from the digitized and interpolated quadrature output signals are analyzed as a function of the applied force to calculate viscoelastic properties of a sample of material.

53 Claims, 12 Drawing Sheets

DYNAMIC AND THERMAL MECHANICAL ANALYZER HAVING AN OPTICAL ENCODER WITH DIFFRACTION GRATING AND A LINEAR PERMANENT MAGNET MOTOR

BACKGROUND

1. Field of the Invention

The present invention relates to thermal analytic apparatus such as dynamical mechanical analyzers (DMAs) and thermal mechanical analyzers (TMAs).

2. Background of the Invention.

Dynamical Mechanical Analysis

Dynamic mechanical analysis is a technique for measuring the viscoelastic properties of materials by applying a periodic load to a sample of the material. DMA measures material properties such as the modulus of elasticity and the damping. Measurement of such properties provides quantitative and qualitative information about the performance of the sample material.

A wide variety of materials may be evaluated using DMA including, for example, elastomers, viscous thermoset liquids, composites, coatings and adhesives, ceramics and metals. DMA is also widely used to evaluate viscoelastic polymeric materials which exhibit time-dependent, frequency-dependent and temperature-dependent effects on their mechanical properties. DMA may also be used to study physical transformations relating to changes in the structure of the material, by analyzing the change of properties such as modulus of elasticity or damping as a function of time, temperature or frequency.

A typical transformation that can be studied using DMA is the glass transition, in which a material such as a polymer changes from a well-ordered crystalline structure to an amorphous or glassy structure. DMA can also be used to study time-dependent material properties, such as creep (a long term deformation of the sample under constant load) and stress relaxation (the reduction of stress in a sample subjected to a constant initial deformation).

DMAs generally include fixtures that hold the sample in one of a variety of testing configurations; a drive that applies a periodic load to the sample; means for measuring the displacement of the sample as a function of the applied load; a sample chamber to heat, cool and protect the sample; a control system to apply the loads and regulate the temperature; and a data collection system to record the measurements.

The fixtures include clamps which hold the sample. At least one of the clamps is movable with respect to at least one other clamp, so that the sample may be deformed. The movable clamp (clamps) is (are) connected to the drive system which can move the sample by a predetermined displacement, or apply a load of a predetermined magnitude and direction. DMAs deform samples in a variety of modes by using interchangeable fixtures. Typical different deformation modes include flexure, tension, compression and shear modes.

In DMAs, the displacement applied to the sample varies periodically, usually sinusoidally. The oscillation frequencies typically ranges from 0.001 Hz to 100 Hz or above. The force required to cause this displacement is recorded along with the displacement and the phase relationship between the load and the displacement.

The sample and the fixtures are enclosed within a temperature-controlled sample chamber which can heat the sample and the fixtures to temperatures above normal ambient temperatures or cool the sample and the fixtures to temperatures below normal ambient temperatures. The temperature is generally varied dynamically, e.g., at a constant heating or cooling rate.

The stiffness and damping of the sample are then calculated as a function of temperature from the force, displacement and phase data, using well-known mathematical relationships which separate the applied load into the components due to movement of the mechanical system and the components due to deformation of the sample. The phase relationship between the force applied to the sample and the resultant displacement allows the sample deformation force component to be further divided into an elastic component and a viscous component. The elastic and viscous components are used to determine the elastic modulus and damping through the use of model equations for the particular sample geometry and deformation mode. These equations are well-known in the field, e.g., Theory of Elasticity, S. P. Timoshenko and J. N. Goodier, McGraw-Hill (3rd ed. 1970).

Thermal Mechanical Analysis

Thermal Mechanical Analysis is a technique for measuring the linear or volumetric change in the dimensions of a sample as a function of time, temperature or force. The coefficient of thermal expansion, viscosity, gel time and temperature, glass transition temperature and other properties of the sample can be determined from this data. Furthermore, physical transformations of a sample may be studied by analyzing the record of the load and deformation as a function of time. TMA can be used to determine the properties of the same wide variety of materials that can be analyzed using DMA. A typical prior art TMA is described in U.S. Pat. No. 4,019,365 to Woo.

Thermal Mechanical Analyzers are similar to DMAs in that a sample is held by a set of fixtures, a load is applied by a drive system, the applied load and the consequent displacement of the sample are measured and recorded as the sample and the fixtures are heated or cooled at controlled heating or cooling rates. Also like DMA, TMA uses a set of interchangeable fixtures to impose a variety of different deformation modes upon the sample, including the flexure, tension, shear and compression modes. Unlike DMA, however, the load applied to the sample in TMA does not vary periodically with time.

Because DMA and TMA have many components in common, some instruments, including the present invention, can perform both types of analyses. The term "mechanical analyzer" will be used herein to refer to dynamic mechanical analyzers, or thermal mechanical analyzers, or both dynamic and thermal mechanical analyzers, or to instruments that can be used for both dynamic and thermal mechanical analysis.

The Drive System

The drive system of a DMA/TMA consists of a guidance mechanism, a motor and a displacement sensor.

The guidance mechanism must ensure that the drive is linear, must allow the desired range of motion, and must be highly reproducible. Guidance mechanisms use either bearings or elastic flexures to guide the drive. Two types of bearings have been used in the prior art, air bearings and jewel bearings. Air bearings have much lower friction than jewel bearings, but typically have much higher mass and are more expensive. Because of their higher friction, systems using jewel bearings cannot be as well calibrated, and accordingly have reduced force resolution. They cannot be used for very low stiffness samples and have reduced precision (because they cannot be as well calibrated) when running higher stiffness samples. Guidance mechanisms using elastic flexures cannot accurately measure the properties of low stiffness samples, and have a limited range of motion (typically on the order of 1 mm or less).

The motors typically used for DMA/TMA systems are linear permanent magnet motors. These motors comprise a fixed permanent magnet and a moving coil assembly. The field strength of permanent magnets decreases with increasing temperature. Thus changes in temperature in the magnets from heat generation in the moving coil assembly reduce the force output of the motor. This causes errors in the measurement of the force applied to the sample. Furthermore, the flexible leads which supply electrical current to the moving coil assembly exert a force which can cause errors in the displacement measurement. Best results are obtained using very flexible leads, which exert the least force.

Prior art DMAs and TMAs have used linear variable differential transformers ("LVDTs") and eddy current transducers as displacement transducers to measure the displacement of the drive system. LVDTs have the disadvantage that the resolution is inversely proportional to the measurement stroke so that the highest precision is obtained with the shortest stroke. Stray magnetic fields from the DMA or TMA electronics, drive motor and furnace can cause errors in the displacement measurement. This susceptibility to magnetic field and limited range of displacement for high precision are the major drawbacks to systems using the LVDT.

Single coil eddy current transducers are very nonlinear, and therefore require very careful linearization for displacement readings. Dual coil eddy current transducers are reasonably linear, but require access to both sides of the target conductive material, and are therefore more complicated mechanically.

The displacement transducer can be affected by incidental movements of the drive frame, which is the fixed part of the instrument. There are two principal causes of these incidental movements: differential thermal expansion, and support vibration effects due to motion of the drive frame. Thermal expansion effects occur over a long period of time compared to the frequency of oscillation, and generally result in a long term drift in the position measurement. Support effects allow the frame to vibrate at the drive frequency. Because the displacement transducer is on the frame, frame movement contributes to the measured displacement. The phase of the frame movement varies from in phase to 180° out of phase, depending on the drive frequency, the natural frequency of the sample, and the natural frequency of the support. The result is that the displacement of the sample may be slightly smaller, or slightly larger than the measured displacement. Thus, when the portion of the drive force attributed to acceleration of the moving part of the instrument is calculated, it will be either high or low, with the result that the sample properties will be in error.

If the drive frequency is in resonance with a natural frequency of the mechanical system, the support vibration effects are particularly troublesome. They produce a peak in the sample properties which may be erroneously interpreted as a physical transformation in the sample. Thus the instrument must be designed such that it can account for both of thermal expansion and vibration support displacement errors, to achieve maximum precision.

The Sample Chamber

The sample chamber heats or cools the sample, and provides a protective atmosphere to prevent sample degradation. Resistive heating elements can be located within the sample enclosure heating the sample and its fixtures directly, or they can be located external to the sample enclosure, heating air which is passed through the sample enclosure by a fan.

The sample and fixtures are cooled by introducing a cryogenic liquid or gas, generally nitrogen, into the sample chamber. When the cooling medium is a gas, the liquid cryogen is evaporated external to the sample chamber and the cold gas is transmitted to the sample chamber. When the cooling medium is a liquid, the liquid cryogen is transmitted to the sample chamber where it evaporates and cools the sample and its fixtures. Because the evaporation of a cryogenic liquid absorbs a large quantity of energy, a much greater cooling effect is available when using evaporation of the cryogen within the sample chamber, leading to a much lower consumption of the cryogen. Unfortunately, the difference in temperature between the liquid and the gas is large, so that the evaporation process can cause large temperature variations within the sample chamber, which in turn can cause large and erratic variations of the sample temperature.

Because DMAs are often operated at temperatures well below room temperature, condensation of atmospheric moisture within the sample chamber can occur. In most cases, the sample region is purged with a dry gas to prevent this moisture from contaminating the sample. Current DMAs use fibrous thermal insulation to maintain the low or high temperature of the sample region. Although this is a very effective thermal insulator, it also absorbs moisture from atmospheric condensation very readily. When the sample chamber is cooled, this moisture freezes, forming ice which reduces the effectiveness of the insulation. Later on, when the DMA is heated up, the ice melts and may drip into the sample region and may contaminate the sample.

SUMMARY OF THE INVENTION

The present invention is a mechanical analyzer that can be used for either dynamic mechanical analysis or thermal mechanical analysis. The mechanical analyzer uses a linear motor comprising a permanent magnet and a moving coil. The linear motor drives a slide guided by two sets of air bearings within a box-like frame. At least one segment of a sample is clamped onto a movable sample fixture rigidly attached to the slide, and at least one other segment of the sample is rigidly attached to a fixed frame. Sample fixture 15 is located within sample zone 21. Sample zone 21 is enclosed by the heating and cooling assembly described below.

Air bearings, as used in the summary of the invention section and in the detailed description of the invention section of this specification, as well as in the claims, is not restricted to bearings which use air as the gas in the bearing. As is known in the art, other gases including nitrogen could be used in air bearings. Accordingly, the term "air bearings" shall mean any type of bearing which uses a gas, such as air, nitrogen, or any other gas, to provide support to a surface.

An optical position transducer comprising a diffraction grating mounted on the slide and a light source and a photodetector system mounted on the frame is used to measure the position of the slide. A light beam emitted by the light source is reflected by the diffraction grating. The reflected beam is focussed upon a photodetector system, which produces two quadrature output signals. The two quadrature output signals are converted to eight-bit digital signals by analog-to-digital converters. These two eight-bit digital signals are then supplied to a lookup EPROM, where they are converted to ten-bit angle and six-bit magnitude digital signals for subsequent digital signal processing.

A digital signal processor reads the position of the slide, using a ten-bit digital signal. A set of ten sequential values is processed by summing up the ten values, looking up the sine and cosine values of the drive signal and then placing the sine, cosine, and position sums into a circular queue for a dual port RAM.

A microprocessor reads these values from the dual port RAM queue and uses them to calculate data points twice each second. The data calculated includes an average position and a single point Fourier transform of that position. The Fourier transform results are the magnitude of sample oscillation and the phase relative to the drive signal.

The Fourier transform also processes the position readings to calculate the magnitude and phase of sample oscillation. This process is a little more complicated since it involves multiplying each ten-point average by a sine and a cosine value before summing the results and then finding the square root of the sum of the squares for the magnitude and the arc tangent of the ratio for the phase.

The measured amplitude of oscillation of the sample and the phase of that oscillation relative to the drive force applied to the sample, along with the oscillation drive force applied to the sample, are used to calculate the storage modulus and the loss modulus of the sample.

DETAILED DESCRIPTION OF THE INVENTION

The present invention is described in detail herein in terms of a single specific preferred embodiment of the invention. However, one skilled in the art could readily practice the invention using variations or modifications of the embodiment described herein.

Overall Description

Figure 1:
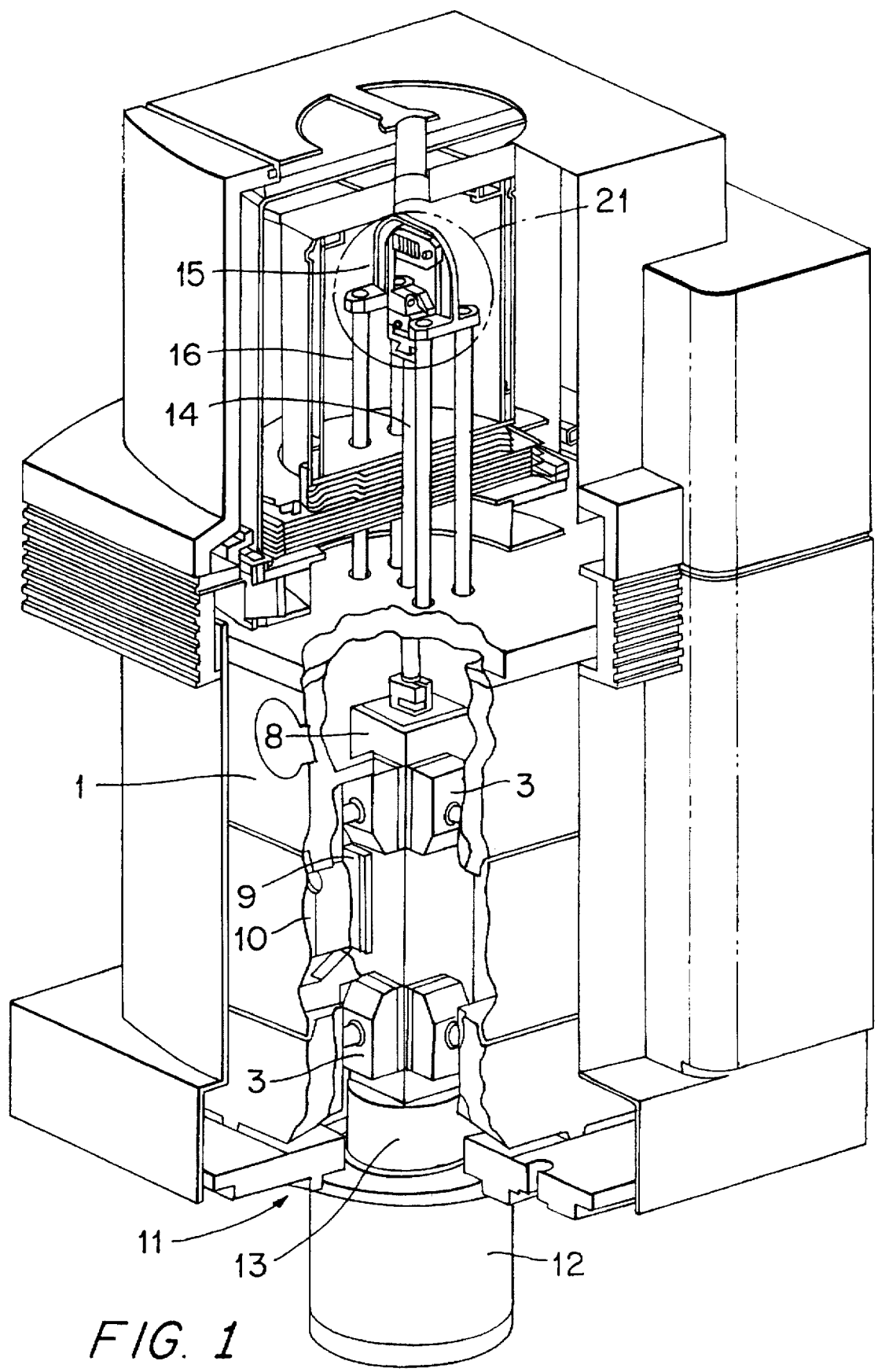
FIG. 1 is schematic a perspective schematic cutaway view of present invention.

FIG. 1 is an overall view of the present invention showing frame 1 supporting air bearings 3, which guide slide 8. Diffraction grating 9 is mounted to the slide. Optical transducer 10, which reads optical signals reflected from diffraction grating 9 is attached to frame 1. Motor assembly 11, includes permanent magnet assembly 12 attached to frame 1, and moving coil assembly 13 attached to the bottom of slide 8. Drive rod 14 connects slide 8 to the moving part of sample fixture 15. The nonmoving part of the sample fixture is supported by posts 16.

Figure 2:
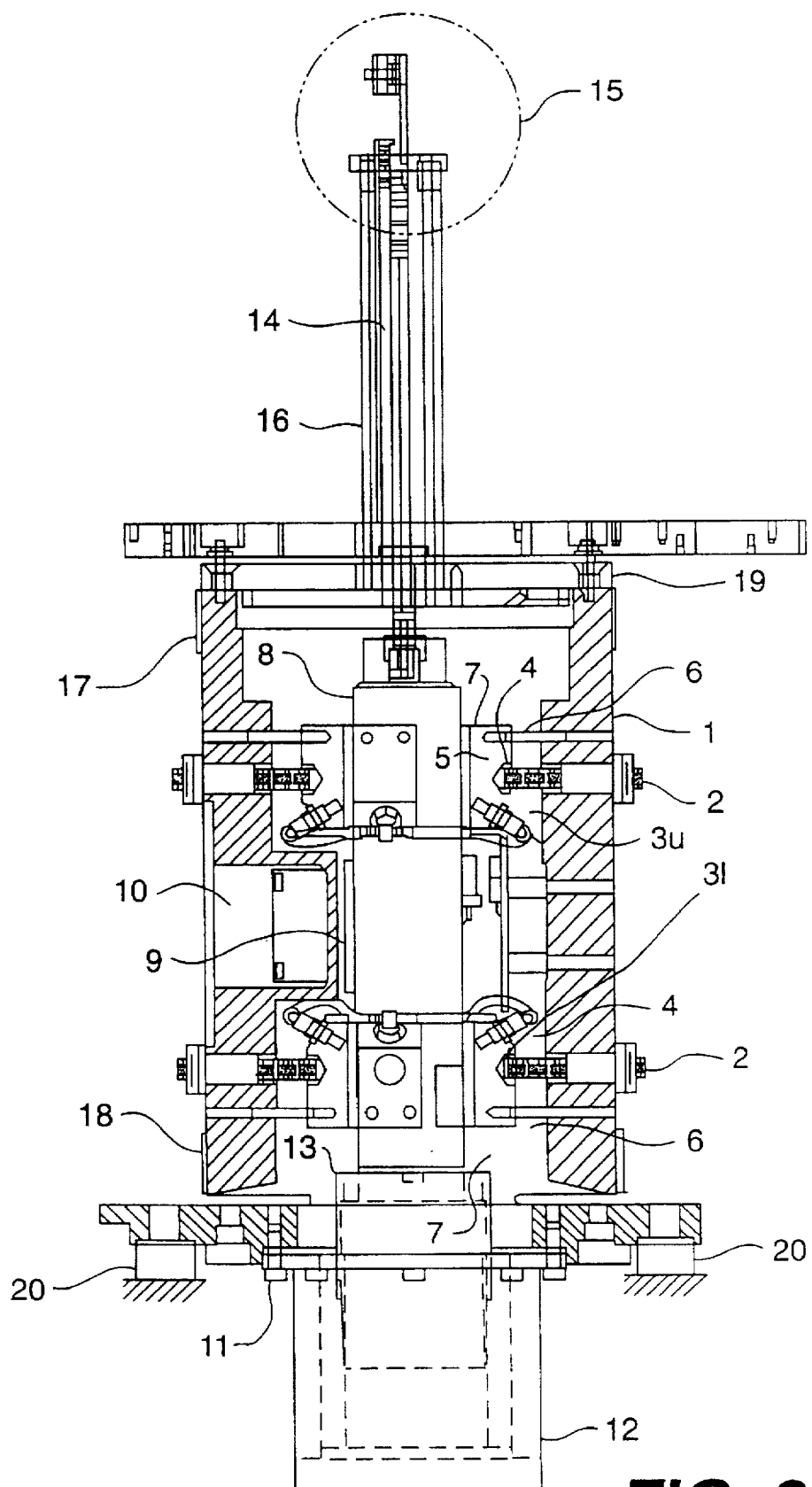
FIG. 2 is a schematic vertical cross sectional diagram of the drive system of the present invention.

FIG. 2 is a vertical cross sectional view taken through the midplane of the drive assembly. Box-shaped frame structure 1 has eight adjusting screws 2 mounted at eight locations, four upper adjusting screws and four lower adjusting screws. Each of the four upper adjusting screws have their centerlines in a common upper horizontal plane, and each of the four lower adjusting screws have their centerlines in a common horizontal plane. There is one upper and one lower horizontal screw on each side of box-like frame 1. The four upper adjusting screws support four upper plane air bearings 3u, and the four lower adjusting screws support four lower plane air bearings 3l.

The end 4 of each adjusting screw 2 is spherical, and engages a corresponding conical cavity 5 in the corresponding air bearing. Spherical end 4 and conical cavity 5 allow air bearings 3u and 3l to pivot about the end of adjusting screws 2, allowing the bearings to align themselves against the surface of slide 8. Air bearings 3u and 3l are prevented from rotating about the axis of adjusting screws 2 by locating pins 6, which are installed in the frame adjacent to each of adjusting screws 2. Each locating pin engages a corresponding hole 7 in the corresponding air bearing 3. The holes are larger than pin 6, so that pins 6 do not restrict the alignment of the bearing to the surface of slide 8.

Air bearings 3 surround and guide slide 8. Slide 8 is also box shaped, with a square cross section normal to the drive direction. Air bearings 3 guide slide 8 on the four planes on the four sides of slide 8, with one upper air bearing 3u and one lower air bearing 3l contacting each of the four planes. The eight air bearings 3 are arranged to constrain the slide so that it has only one degree of freedom, along its longitudinal axis. Thus the air bearings provide a very low friction guide for slide 8, over a relatively long, e.g., 25 mm, stroke.

The present invention is described in terms of an embodiment which uses two sets of four air bearings to guide a box-shaped slide. However, other types of air beatings and slides could also be used. For example, two circular air bearings or a single cylindrical air bearing could be used in conjunction with a cylindrical slide, or two sets of six air bearings could be used in conjunction with a hexagonal slide. If a cylindrical slide were used, it would have to use a slot and key mechanism to prevent the slide from rotating within the bearing. Elliptical air bearings could also be used in conjunction with an elliptical slide.

A diffraction grating 9 with highly accurate and very closely spaced rulings is mounted to the slide so that it moves with the slide. An optical encoder 10, e.g., a Heidenhain Model No. LIF101 encoder distributed by the Heidenhain Corporation, Schaumburg, Ill., is mounted to the frame (see FIG. 13A, discussed below).

The intensity of the beam incident upon the photodetector system is modulated by the diffraction grating as it moves along with the slide. The output of the photodetector system accordingly consists of a series of pulses. Counting the number of pulses as slide 8 moves provides the distance the slide has moved. Thus optical encoder 10 is a relative position sensing system which measures the change in position of slide 8 by counting the pulses produced as the beam reflects off diffraction grating 9, as slide 8 moves from one position to another. The electronics system supporting the optical encoder keeps track of the pulse count, to provide an absolute position measurement.

Linear motor 11 is comprised mainly of permanent magnet 12 and moving coil assembly 13. Moving coil assembly 13 is rigidly attached to the bottom end of slide 8, and permanent magnet 12 is attached to frame 1. Direct current applied to moving coil assembly 13 causes moving coil assembly 13 to apply a force to slide 8 proportional to the current, with a direction corresponding to the polarity of the current.

Drive rod 14 is attached at its bottom end to the top end of slide 8, and at a its top end to the moving part of the sample fixture 15. The nonmoving part of the sample fixture is attached to four support posts 16 surrounding drive rod 14. These posts are, in turn, connected to thermal compensating plate 19 (described below) which is attached to the top of frame 1. The sample is mounted between the moving and the non-moving parts of the fixture.

Drive rod 14, sample fixture 15 and the supporting structure for the fixed clamp assembly (e.g., support posts 16 on FIGS. 1 and 2) are preferably made of stainless steel for DMA and of quartz for TMA.

In operation, when a DC current flows through the winding of moving coil assembly 13, moving coil assembly 13 applies a force to slide 8. The force is transmitted to the sample through drive rod 14 through the moving part of sample fixture 15 to the sample. The sample is deformed by the motion of the moving clamp and the resulting displacement is measured by optical encoder 10.

Temperature Compensation

To minimize any errors caused by differential thermal expansion of the drive assembly components, the drive frame is heated to a temperature above ambient and maintained at that temperature by a temperature regulation system. The temperature increase is relatively large, so that the temperature of the drive frame can be regulated despite the heat generated within the instrument, or by increases in the surrounding temperature. A resistance heating element 17 is mounted to, and surrounds a portion of the drive frame near the top and a second identical heating element 18 is mounted to, and surrounds a portion of the drive frame near the bottom. Temperature sensors mounted to the frame supply the frame temperature to a power controller, which regulates the heating current to heaters 17 and 18 so as to maintain a constant frame temperature. At the top of the drive frame, thermal compensating plate 19 is attached to the frame and closes the frame at the top. Thermal compensating plate 19 is a thick high thermal conductivity metal plate which ensures that the frame, and the instrument components within the frame, are a closed isothermal system, such that the slide and the air bearings are maintained at the same temperature as the frame.

Vibration Isolation

To prevent the dynamic motion of the drive supports and vibrations upon the instrument's mounting surface from affecting the displacement measurement, the frame assembly is mounted on elastomeric vibration isolation mounts 20. The frequencies of support resonances due to the cabinet the drive assembly is mounted in, or to the work benches the instrument is placed on, have typically been found to be above 100 Hz. Accordingly, the characteristics of the isolator have been chosen such that the natural frequency of the drive assembly on the isolators is well below 100 Hz to achieve effective isolation of the drive assembly from the cabinet and the work benches. However, any movement of the drive assembly on the isolators affects the displacement measurement by allowing the frame assembly to move under the action of the drive force. Because the behavior of the isolator system is very reproducible, it can be compensated for by calibration of the instrument.

Air Bearing Support

Figure 3:
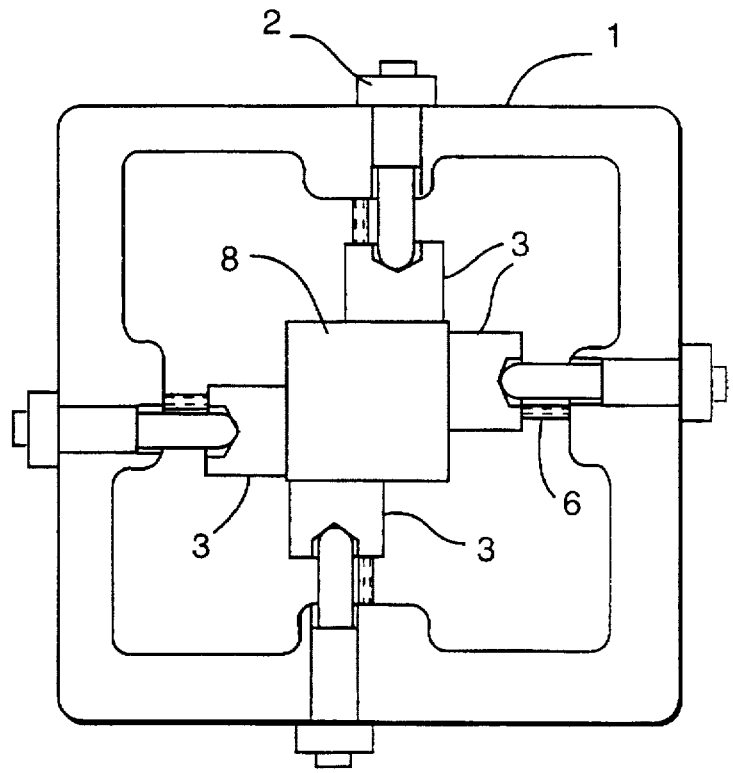
FIG. 3 is a schematic horizontal cross sectional diagram of the frame assembly.

FIG. 3 is a horizontal cross section through the drive assembly taken at a plane of the adjusting screws. Adjusting screws 2 are mounted in frame 1, one each through each of the four sides of the frame. Each adjusting screw 2 supports and locates an air bearing 3. A locating pin 6 is mounted in the frame adjacent to each of the adjusting screws and prevents the air bearing from rotating about the adjusting screw axis. Air bearings 3 allow slide 8 to move only along its longitudinal axis.

Heating and Cooling Assemblies

Figure 4:
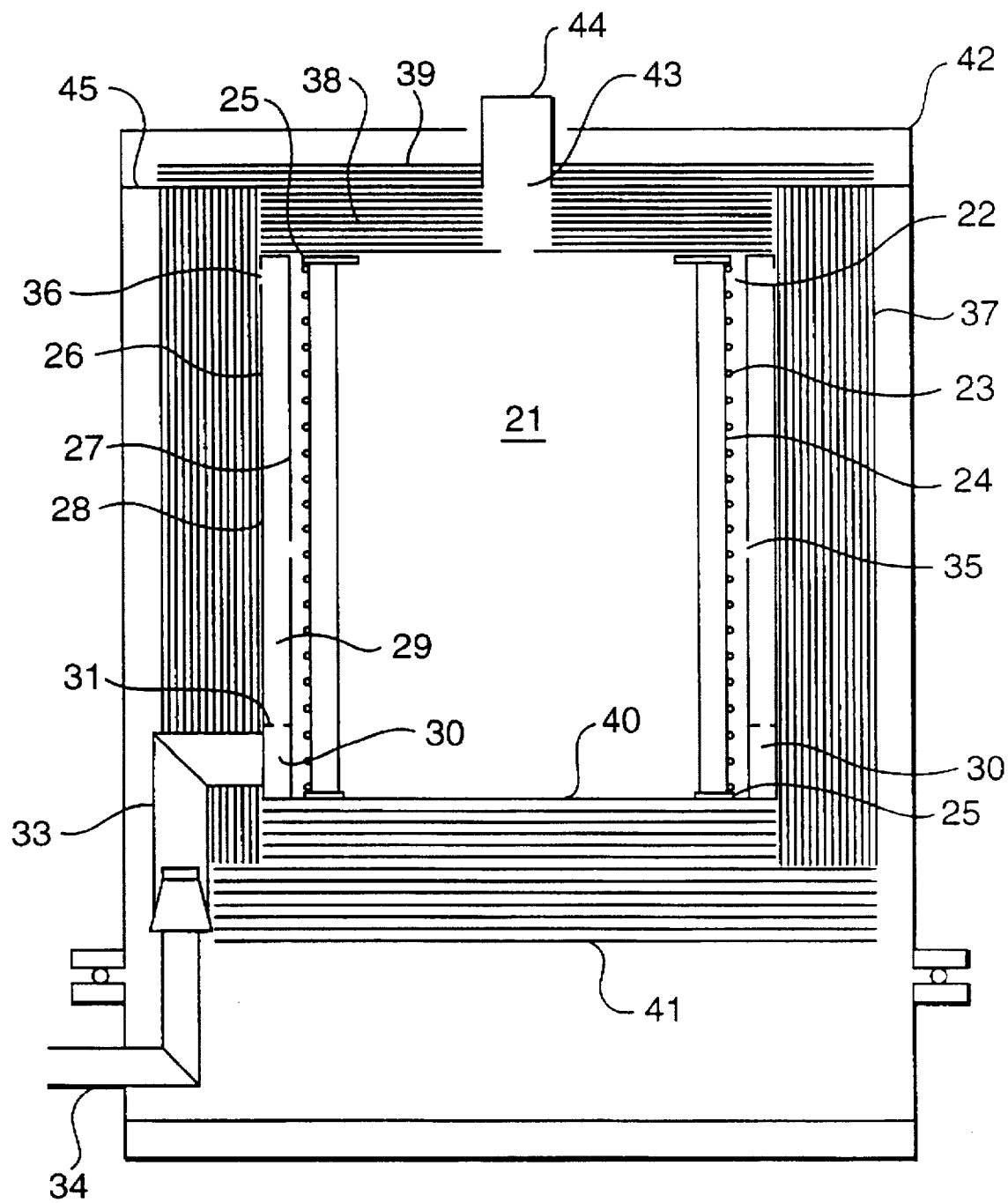
FIG. 4 is a schematic vertical cross sectional diagram of the furnace assembly.

FIG. 4 is a vertical cross section through the centerline of the sample chamber. Sample zone 21 is surrounded by a heating assembly 22 comprised of a resistive heating element 23 which is wound in a helix around eight ceramic insulator rods 24. The insulator rods are connected at each of their ends to rings 25, thus forming a cage-like heater assembly. An electric current flowing through heating element 23 generates heat by Joule heating. The heat is transmitted to the sample zone by radiation, conduction and convection.

Heating assembly 22 is surrounded by cooling jacket 26. Cooling jacket 26 is comprised of inner cylinder 27 and outer cylinder 28—the inner and outer cylinders being connected at their extremities to form an annular cavity. The annular cavity is divided into an upper chamber 29 and a lower chamber 30 by divider 31. Divider 31 is perforated by a series of holes uniformly distributed about its middle circumference. Cooling gas is supplied to the lower chamber 30 through the gas supply tube 33, which is supplied by the connector 34. Gas passes from the lower chamber to the upper chamber through the holes in the divider. The cooling gas flows upward in the upper chamber 29 of cooling jacket 26, cooling the sample chamber. A small fraction of the cooling gas is discharged into the sample chamber through a series of small (ranging from 0.035 square inches to 0.060 square inches, preferably 0.043 square inches) holes 35 through the inner wall of the cooling jacket. This small fraction of the cooling gas ensures that the sample environment is adequately cooled and uniform temperature, but is small enough that it will not impose drag forces on thin samples. The remainder of the cooling gas continues upward through the upper chamber of the cooling jacket and exits the cooling jacket through a series of large holes 36 equally spaced around the outer wall of outer cylinder 28.

Cooling jacket 26 is insulated by a coil of thin stainless steel sheet 37. The thickness of the stainless steel sheet is preferably 0.002 inches thick, but it can range from 0.001 inches to 0.005. Stainless steel sheet 37 is wound around cooling jacket 26 in a helical fashion. In some applications, material other than stainless steel could be used. The material must be reflective, and must be otherwise appropriate for the intended temperature range. For example, if the instrument is not intended to be used at relatively high temperatures, the sheet could be an aluminum sheet. If the instrument were intended only for low-temperature operation, a sheet of metallized mylar could be used. Sheet 37, e.g., a 5" high, ten foot long sheet, forms, e.g., fifteen layers which are separated by small protrusions (ranging from 0.02" to 0.125", preferably 0.035", in height), at a density of approximately 0.5 per square inch to 2 per square inch, preferably one per square inch, formed in the stainless steel sheet by stamping. In one embodiment of the present invention, the protrusions are applied along a vertical straight line, but the distance between consecutive straight lines of protrusions is preferably random, such that nesting of one set of protrusions into the dimples formed by the protrusions on a neighboring sheet cannot occur, except in isolated instances.

Stainless steel sheet 37 insulates cooling jacket 26 by preventing heat exchange by radiation and by eliminating convection in the gas spaces between layers. It limits heat transfer to conduction through the gas. Because gases are very poor thermal conductors, the transfer of heat from the ambient to the cooling jacket is low. The spacing of the layers must be kept small enough such that convection cannot develop in the spaces between layers. If the spacing is too large, heat convection will occur and the rate of heat transfer through the gas will increase dramatically—as much as ten times or more. If the spacing is too small, too much stainless steel sheet would have to be used.

The spacing between layers can be increased if the number of layers is increased, which would provide improved insulation. However, this would also result in a system having higher mass, and is therefore less responsive thermally. Thus the speed at which temperature changes could be made would be reduced.

The ends of the sample enclosure are similarly insulated. Disks of thin (0.005 to 0.015 inches thick) stainless steel are stacked to form a multilayer metallic insulation system. At the top end, smaller diameter disks 38 fit inside of the insulation formed by the wound sheet, while larger diameter disks 39 cover the edges of the wound sheet. The overlapping intersection prevents excessive heat loss through the edges of the hottest layers of the heat shielding system. At the bottom of the enclosure, small diameter disks 40 fit inside of the wound heat shield, while larger diameter disks 41 cover the edges of stainless steel sheet 37. The thickness of the disks is dictated by their mechanical properties. The disks must be sufficiently stiff such that they do not vibrate while the instrument is running. However, thicker disks have greater mass, which reduces the instrument's responsiveness.

The entire assembly is enclosed by an outer jacket 42. The cooling gas which is introduced to the sample region exits through an opening 43 through the stack of upper heat shields and then through exhaust stack 44. Cooling gas which exits the cooling jacket at the top flows between the smaller diameter upper heat shields inward to the exhaust stack and then out of the enclosure. To prevent recirculation of the exhausted cooling gas and infiltration of air from the surroundings, one of the large diameter upper shields (which has a larger diameter than the other upper shields) is sealed to the outer jacket.

The metallic shield insulation system described above is very nearly as efficient in preventing heat loss as conventional fibrous insulation systems. Unlike fibrous insulation systems, which have a huge surface area compared with the metallic shield system and are porous, the metallic shield insulation system does not absorb significant quantities of moisture. Furthermore, once moisture is absorbed in a fibrous insulation system, it takes a long time to leave the system. The remaining moisture could contaminate the sample, or could result in water dripping into the sample chamber or elsewhere, or ice formation within the insulation, or elsewhere.

Figure 5:
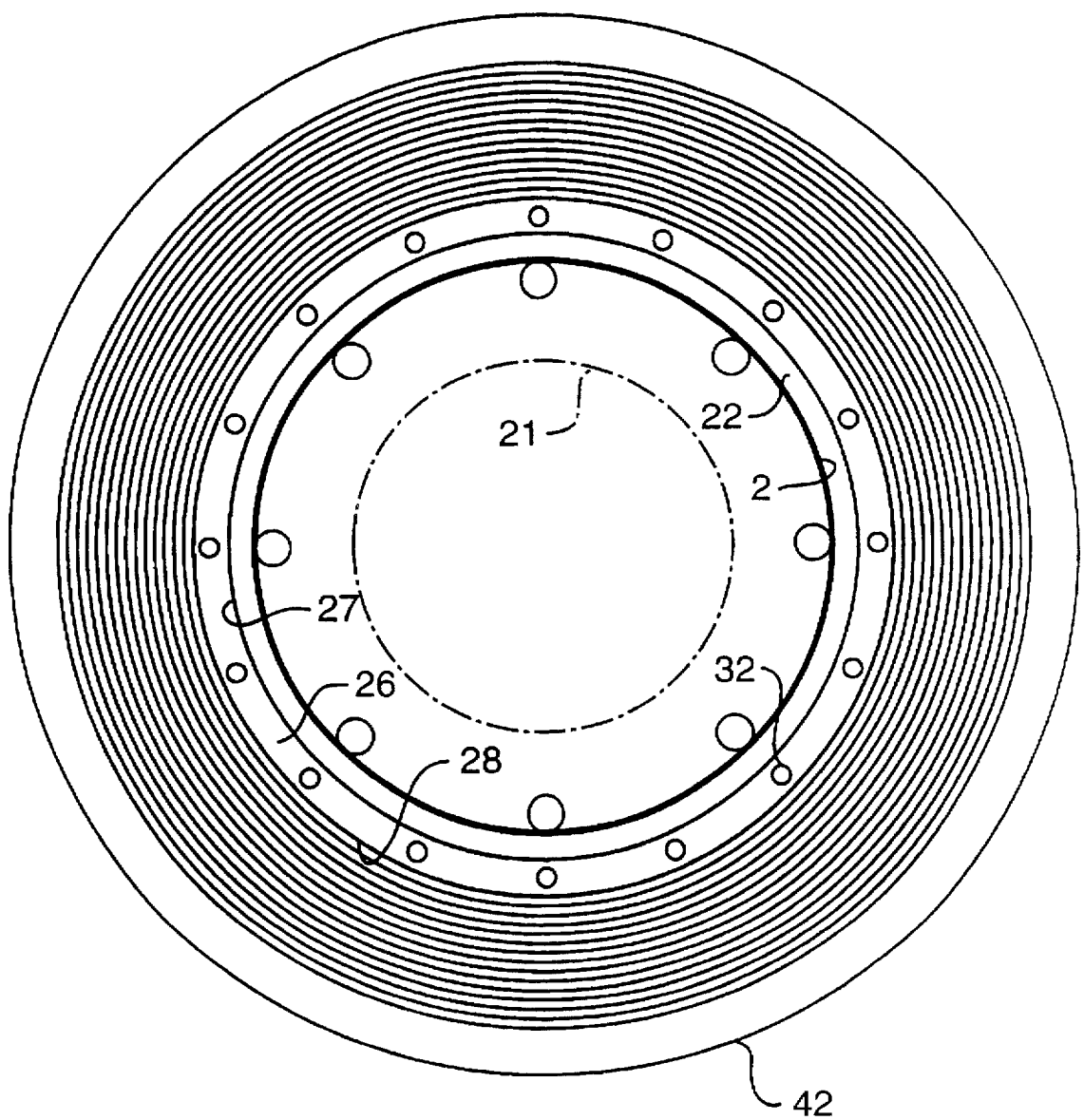
FIG. 5 is a schematic horizontal cross sectional diagram of the sample enclosure.

FIG. 5 is a horizontal cross section through the sample chamber. Sample zone 21 is surrounded by heating assembly 22, which includes resistive heating element 23, wound in a helix around eight ceramic insulator rods 24. The heater assembly is surrounded by the cooling jacket 26, which has inner wall 27 and outer wall 28. Gas flowing from the lower chamber to the upper chamber passes through the series of small holes 32. The total area of the holes through the divider is much smaller than the total cross sectional area of the lower chamber, preferably, less than 10% of the total area. This creates a pressure drop through the holes such that the pressure in the upper chamber is much lower than the pressure in the lower chamber. This ensures that gas flows into the upper chamber with a uniform distribution about the cooling jacket centerline. Coiled thin stainless steel heat shield 37 surrounds the cooling jacket. The heat shields are enclosed within the outer jacket 42.

Linear Motor Assembly

Figure 6:
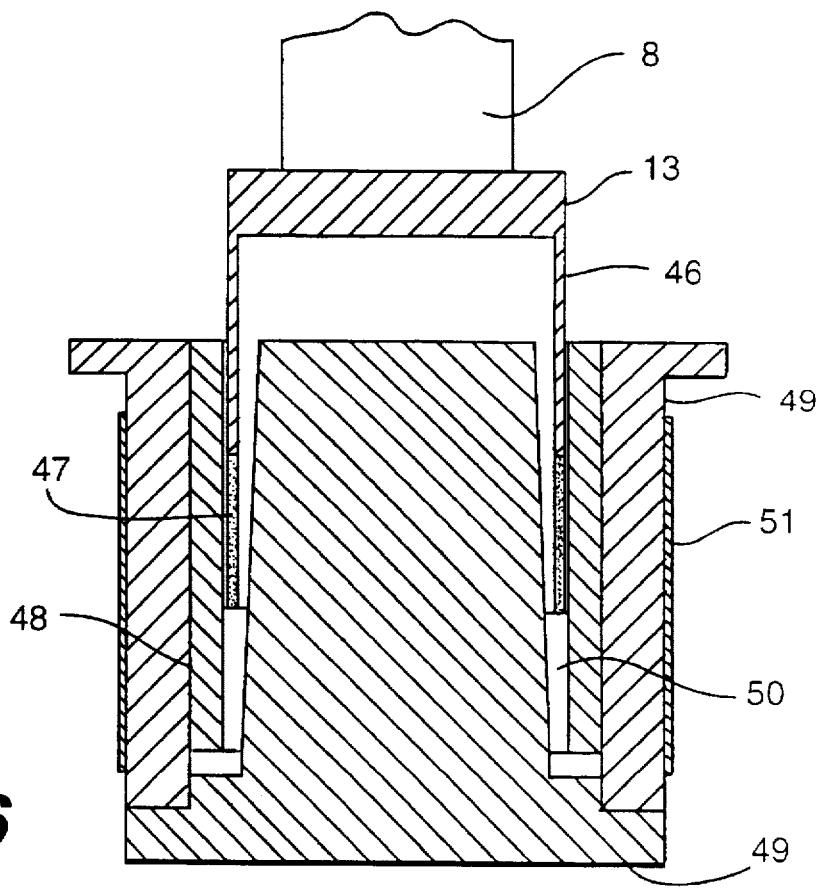
FIG. 6 is a schematic vertical cross sectional diagram of the motor assembly.

FIG. 6 is a vertical cross section through the linear motor assembly. The moving coil assembly 13 consists of a bobbin 46 and a coil or winding 47. Winding 47 is wound around bobbin 46. The top of bobbin 46 is rigidly attached to air bearing slide 8. Winding 47 consists of a large number of turns, e.g, 250 to 280 turns, of fine wire, e.g., 29–30 gauge wire, tightly wound on the bobbin. The force which a motor can develop is proportional to the product of the current and the number of turns in the winding, and also depends on the field strength created in the air gap by the magnet.

The magnet assembly 12 consists of magnet 48, core 49 and air gap 50. In this type of motor, the magnets are magnetized in the direction perpendicular to the motor axis. The core is a high magnetic permeability material, which serves to concentrate the magnetic flux in the air gap by directing the flux from the outer pole of the magnet around and up into the center region of the core. Ideally, the magnetic flux lines across the air gap should be perpendicular to the axis to insure maximum force linearity. Near the ends of the air gap, the flux lines diverge from the ideal path, resulting in magnetic field fringes. If the voice coil windings enter fringing areas, the force drops off rapidly causing excessive nonlinearity. The length of the air gap in the direction parallel to the axis is chosen to be considerably longer than the sum of the length of the winding 47 and the stroke so that no part of winding 47 enters the fringing region during operation.

To improve motor control, it has been found advantageous to have a certain slope to the plot of the motor force versus displacement (which is generally a straight line). The flux density will naturally be greater at the bottom of the air gap where the air gap is closed off by the core. Tapering the air gap slightly so that it is wider at the open end of the magnet assembly than at the closed end enhances the natural slope of the straight line. The taper is created on the inner part of the core because creating a taper on the magnet face would be more difficult.

The strength of the field created by all permanent magnets varies as the temperature of the magnet changes. Variations in field strength cause variations in the force developed by the motor for a given coil current. Thus, it is essential to ensure that the temperature of the magnet and the iron core remain constant. In the present invention, temperature stability is achieved by heating the magnet assembly using a thin ribbon resistance heating element 51 attached to the exterior of the core. The temperature of the core is maintained at a high above-ambient temperature, such that heat generated by the coil does not cause the magnet assembly temperature to rise. A temperature sensor attached to the core supplies the magnet temperature to a power controller, which controls the power to the heater to maintain a constant magnet assembly temperature. However, this control system does not maintain a perfectly constant magnet temperature. Therefore, a second temperature sensor is attached to the core. Input from this second sensor is used to adjust the power to the motor based upon any residual temperature deviations.

Figure 7:
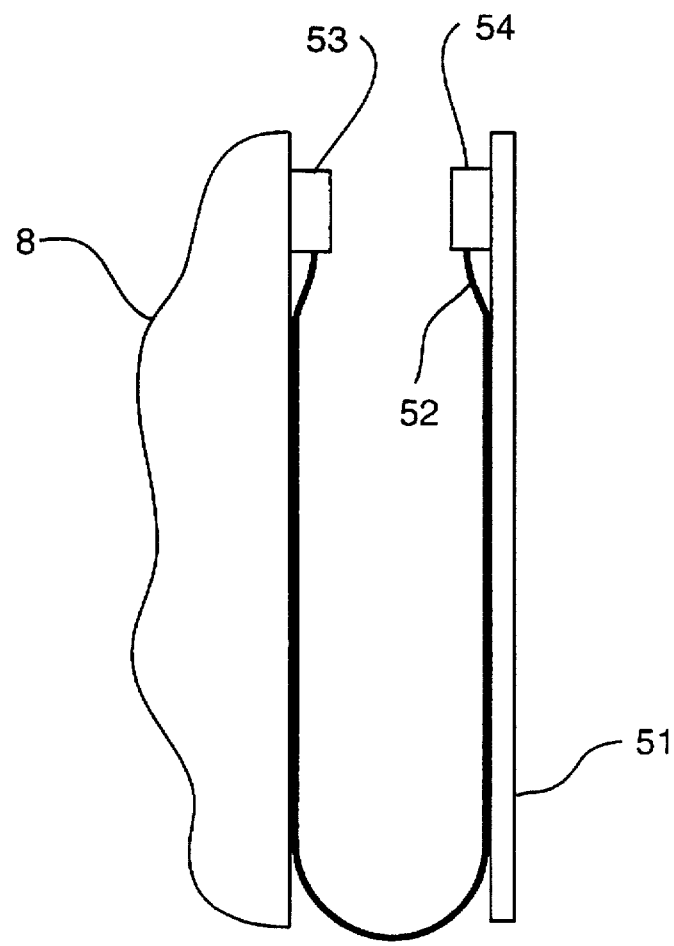
FIG. 7 is a schematic diagram of the moving coil assembly lead wires.

FIG. 7 is a vertical cross-sectional diagram of the configuration of the lead wires which supply electric current to the coil. A pair of flat wires 0.0015" thick by 0.040" wide 52 are arranged side by side. The cross-sectional view in FIG. 7 shows only the thin end of one of the flat wires. The second wire is behind the plane of the figure, and cannot be seen in FIG. 7. The moving end of each wire is attached to a terminal block 53 attached to slide 8, and an extension of the coil leads (not shown) connects to the terminal block. The stationary ends of the wires attach to a second terminal block 54 which is mounted to the wire guide plate 55, which is attached to the drive frame assembly. As the slide moves up and down, the lead wire moves in and out of contact with the slide and the wire guide in a rolling manner so that there is no sliding friction between the wire and either the slide or the guide. Flat wire is used with the thin dimension oriented as shown in FIG. 7 to minimize the force required to flex the wire. The spacing between the slide and the wire guide is chosen to be sufficiently large that flexure of the wire is entirely elastic. This configuration minimizes the force required to flex the lead wires. Because there is no slip and, therefore, no friction resulting from slip, and because the wire flexure is entirely elastic, the force required to flex the lead wires is highly reproducible.

Sample Fixtures

Figure 8:
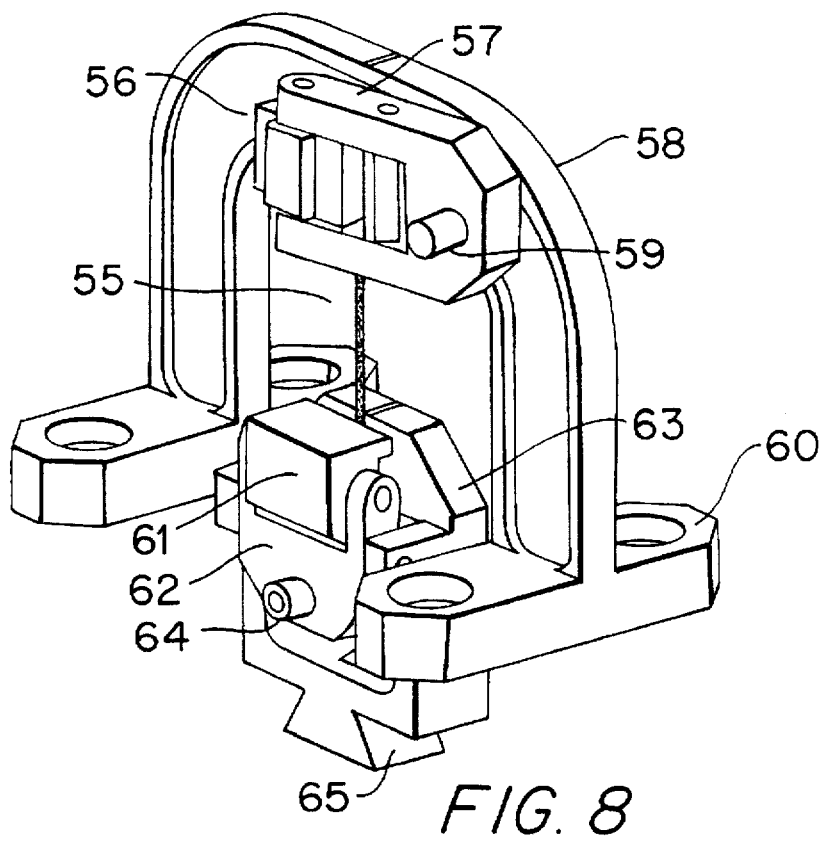
FIG. 8 is a schematic diagram of a tension mode sample clamping fixture.

FIGS. 8–12 show several of the variety of different sample fixtures that can be used with the present invention. FIG. 8 is a diagram of the fixture used for characterizing a fiber or a thin film sample in the tension loading mode. Sample 55 (a fiber in the example illustrated in FIG. 8), is held at the top end by the upper clamp comprised of clamp jaw 56, clamping frame 57 and clamping screw 59. Clamping screw 59 pivots clamping frame 57, driving clamp jaw 56 against the sample. The clamp is attached to stationary frame 58. Stationary frame 58 is attached to support posts 16 through four mounting holes 60. Thus the upper end of the sample is held stationary with respect to frame 1.

The lower end of the sample is clamped to the moving part of the fixture by the lower clamp jaw 61 which is attached through a pivot to clamping frame 62. Clamping frame 62 is mounted on a pivot attached to drive frame 63. Clamping screw 64 pivots clamping frame 62, driving clamp jaw 61 against the sample. Dovetail 65 attached to drive frame 63 engages a complementary dovetail on drive rod 14, thus attaching the moving part of the sample fixture to drive rod 14.

Figure 9:
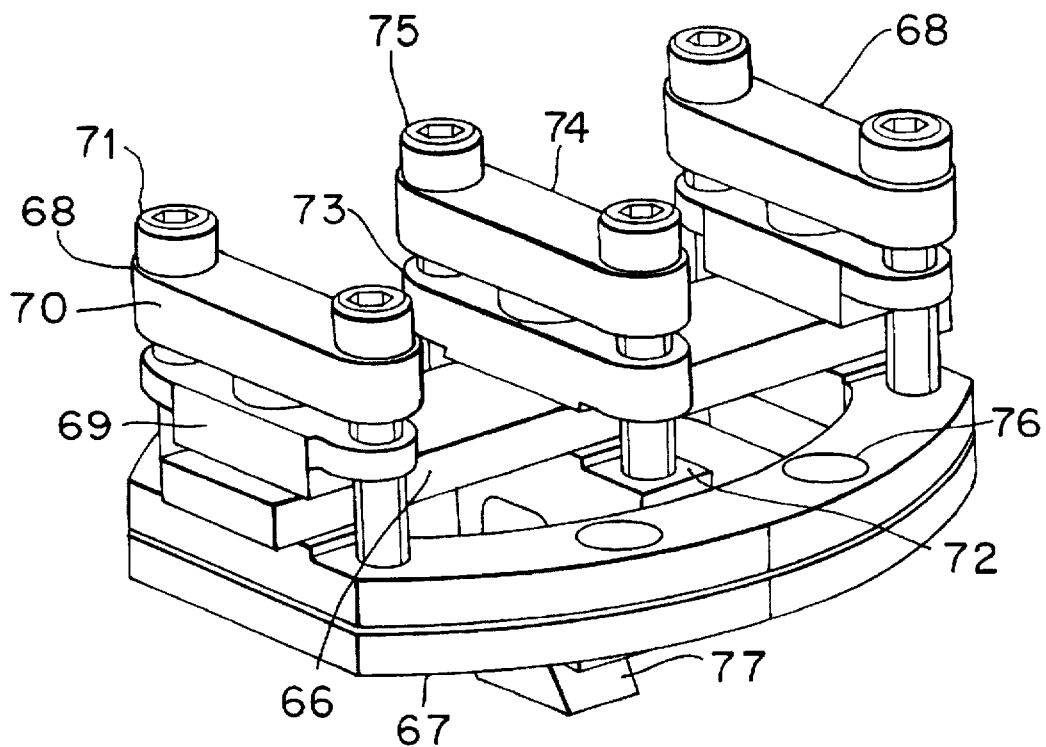
FIG. 9 is a schematic diagram of a dual cantilever flexure mode sample clamping fixture.

FIG. 9 is a schematic diagrams of the fixture for characterizing a sample such as a sheet or a plate in the dual cantilever flexure mode. Sample 66 is clamped to stationary frame 67 near its ends by clamp assemblies 68, which include clamp jaw 69, crosshead 70, and the screws 71. Tightening the screws drives the crosshead down against the clamp jaw, and holds the sample against the drive frame. The crosshead is used to ensure that the clamping load is applied to the center of the clamp jaw so that the clamping load is uniformly distributed across the width of the sample. Stationary frame 67 is attached to vertical supports, e.g., vertical support posts 16 through the four mounting holes 76, holding the ends of the sample stationary with respect to frame 1.

The moving clamp assembly includes drive clamp frame 72, clamp jaw 73, the crosshead 74 and tightening screws 75. Tightening screws 75 drives the crosshead to push the clamp jaw against the sample, clamping the sample against the drive clamping frame, thus holding the sample at its center. Dovetail 77 attached to the drive frame engages with a complementary dovetail on drive rod 14, thus rigidly attaching the moving part of the sample fixture to drive rod 14.

Figure 10:
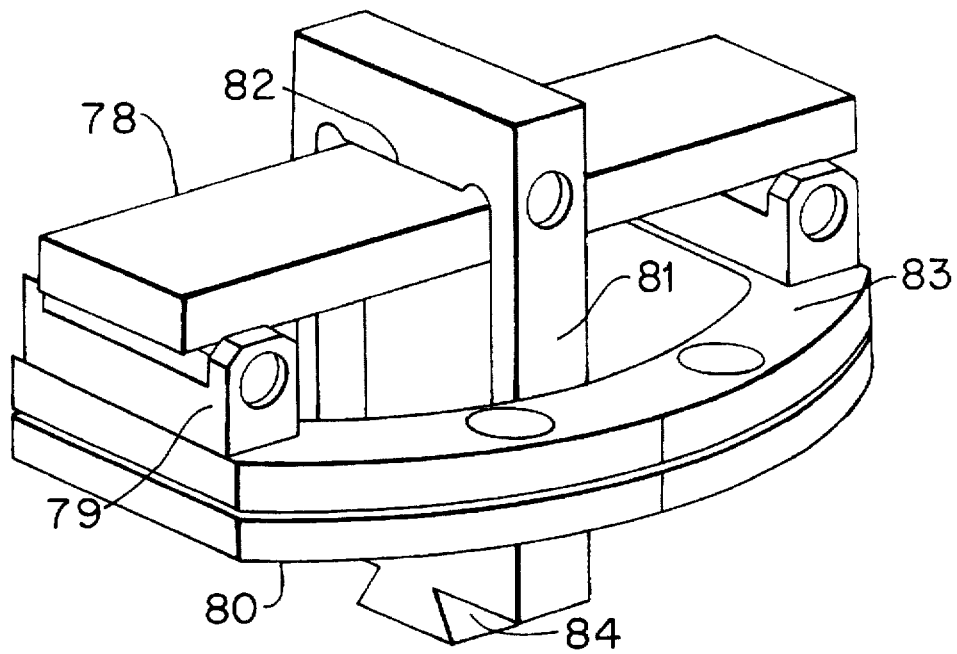
FIG. 10 is a schematic diagram of a 3-point flexure mode sample clamping fixture.

FIG. 10 is a schematic diagram of the fixture used to characterize a sample in the 3-point flexure mode. Sample 78 is supported near its ends by supports 79 which are an integral part of stationary frame 80. A load is applied to the sample at its midpoint by load frame 81, which presses against the sample through an integral load-applying surface 82. Stationary frame 80 is attached to support posts 16 through four mounting holes 83, thus holding the ends of the sample stationary with respect to frame 1. Dovetail 84 attached to the drive frame engages with a complementary dovetail on drive rod 14, attaching the moving part of the fixture to drive rod 14.

Figure 11:
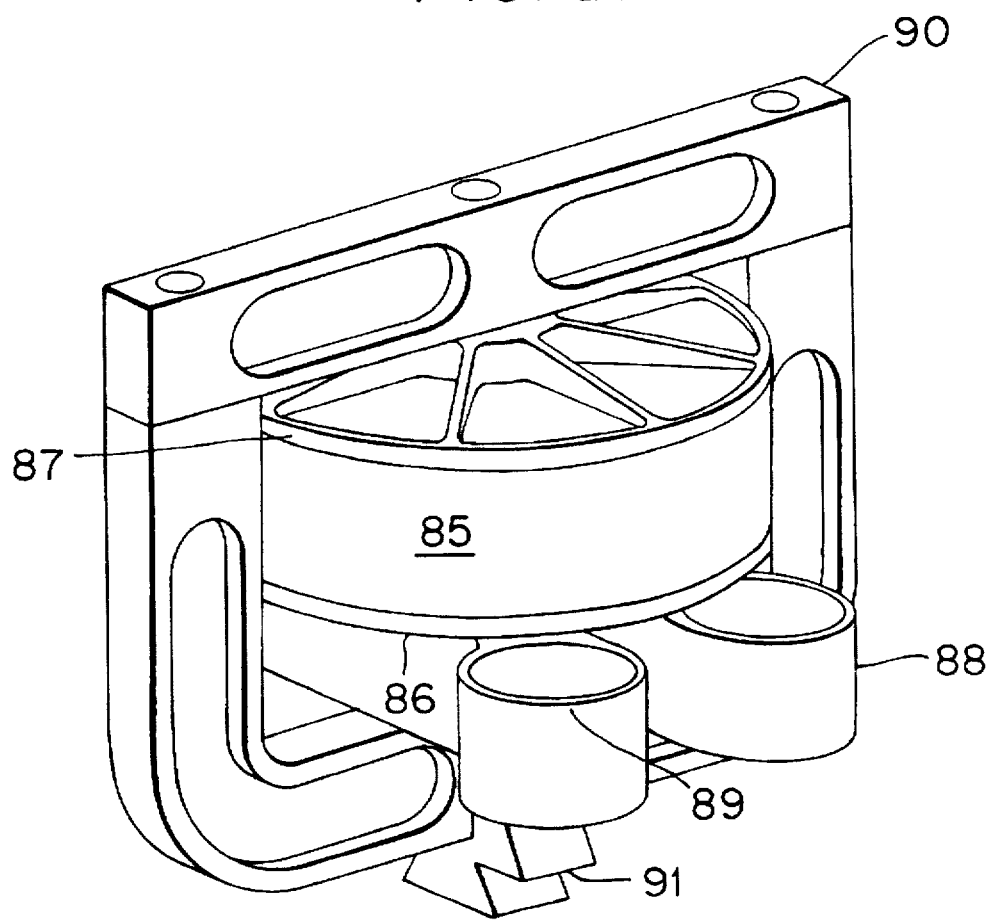
FIG. 11 is a schematic diagram of a compression mode sample fixture.

FIG. 11 is a schematic diagram of the fixture used to characterize a sample in the compression mode. Sample 85 is squeezed under the applied load between the stationary plate 86 and moving plate 87. The stationary plate is attached to the frame 88 which is attached to the support posts 16 through the four mounting holes 89. Moving plate 87 is attached to drive frame 90. A dovetail 91 attached to the drive frame engages with a complementary dovetail on drive rod 14, attaching the moving part of the fixture to drive rod 14.

Figure 12:
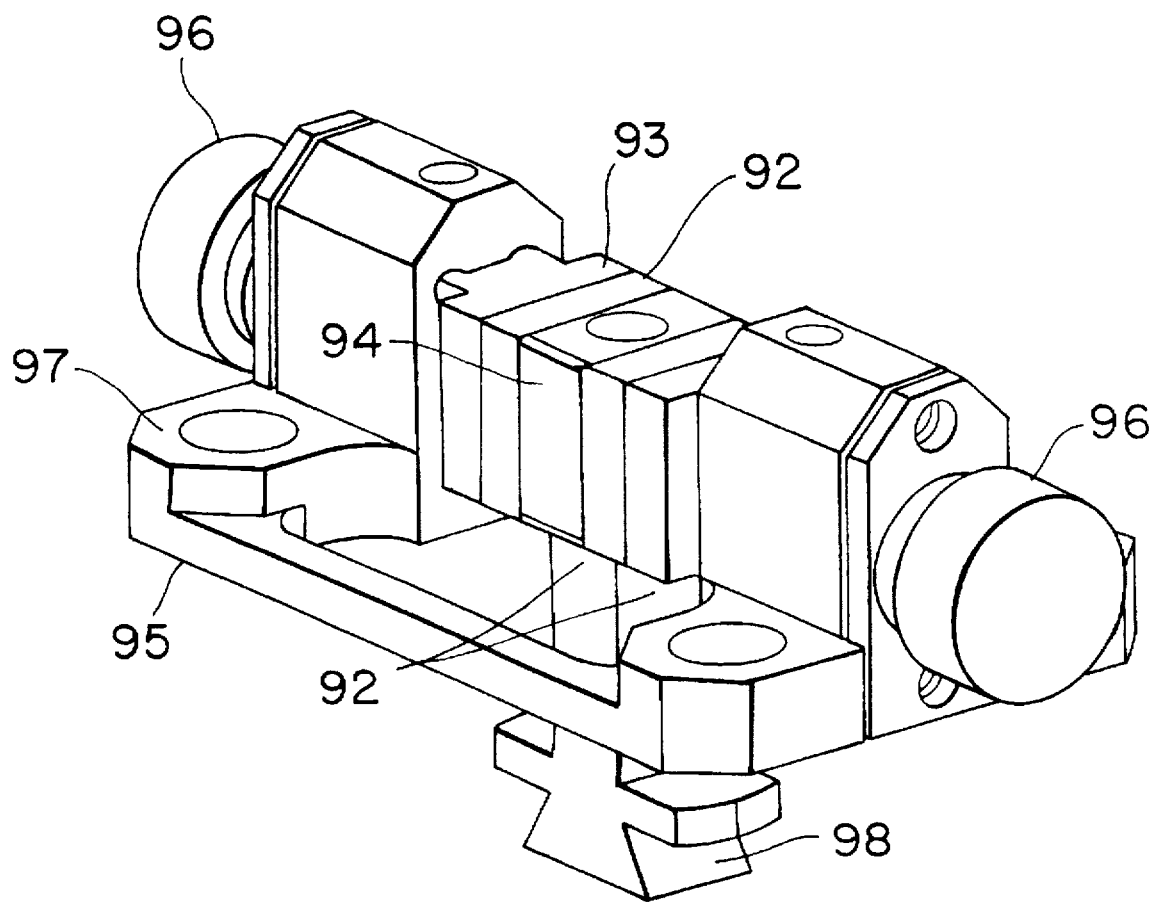
FIG. 12 is a schematic diagram of a shearing mode sample fixture.

FIG. 12 is a schematic diagram of the fixture for characterizing a sample in the shear deformation mode. A pair of identical samples 92 are clamped between opposed movable clamps 93, against the drive plate 94. Drive plate 94 is the sandwiched between the pair of identical samples. Movable clamps 93 are guided by the stationary frame 95 and are driven in and out by thumbscrews 96. Thumbscrews 96 adjust the clamp faces to the sample thickness and apply a compressive load to hold the samples in place. Stationary frame 95 is attached to support posts 16 through the four mounting holes 97, thus holding stationary frame 95 fixed with respect to frame 1. Drive plate 94 is attached to dovetail 98 which engages with a complementary dovetail on drive rod 14, attaching the moving part of the fixture to the drive rod. Thus the samples can be sheared between the clamp faces and the moving plate under the applied load.

The Optical Encoder

Figure 13A:
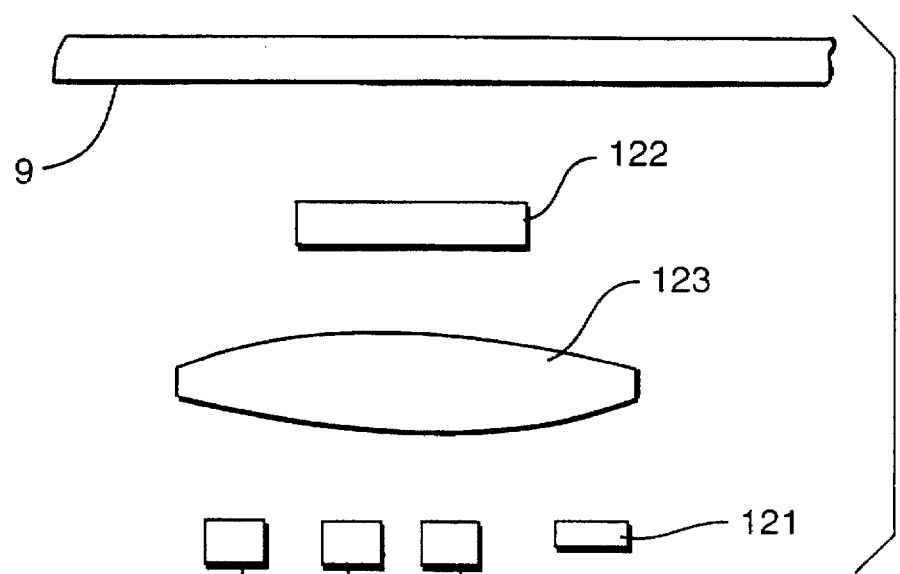
FIG. 13A is a schematic diagram of the optical components of the optical encoder.

FIG. 13A is a schematic diagram of the optical components of optical encoder 10. FIG. 13A shows that the optical components include a diffraction grating 9 (mounted on the slide), LED light source 121, a scanning reticle transparent phase grating 122, condenser lens 123, and photodetector system 124. In the example shown in FIG. 13A, photodetector system 124 includes three photovoltaic cells. A light beam emitted by light source 121 is reflected and modulated by diffraction grating 9, and transmitted and modulated by scanning reticle 122, and detected by photodetector system 101 in encoder 10.

In an instrument built according to the present invention, the spacing between lines on the glass scale diffraction grating was 8 microns. The use of a diffraction grating and light interference results in two constructive maxima and two destructive minima interference lines for each line on the glass scale, i.e., the distance between maxima is 4 microns. Light from LED light source 121 within optical encoder 10 passes through a transparent phase grating, and is reflected off the glass scale back through the phase grating and is focussed on three photovoltaic cells. The signals from these photovoltaic cells are combined by the Heidenhain electronic circuits to produce two quadrature output signals.

Figure 13B:
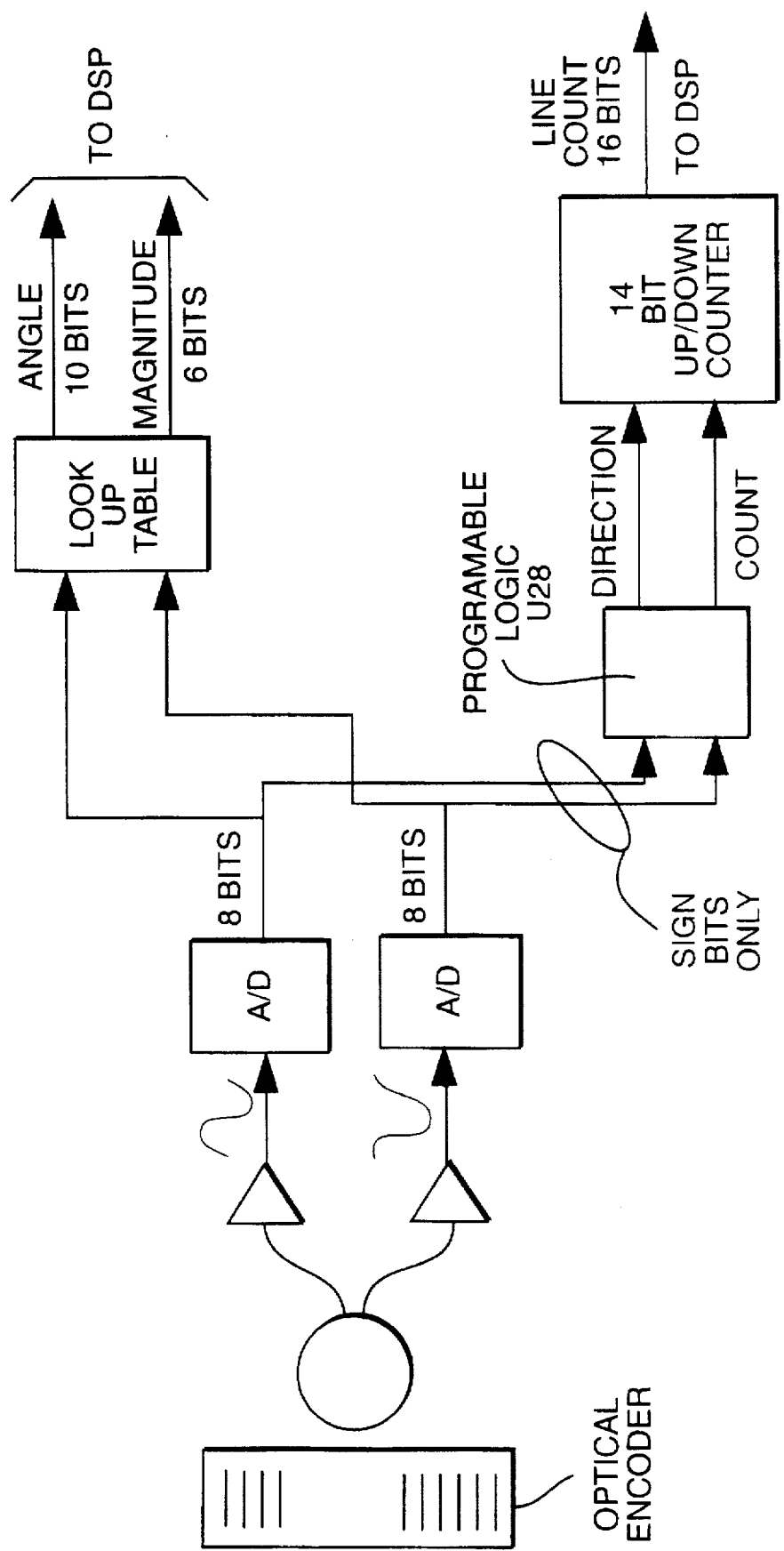
FIG. 13B is a schematic block diagram of the optical encoder electronic signal processing.

FIG. 13B is a schematic diagram of system for processing the photodetector system output signal. Photodetector system 101 produces two output signals, as shown after amplification by instrumentation amplifiers 102, e.g., Burr-Brown INA103, in FIG. 13B, which are in quadrature with respect to each other. The optical period of the two quadrature output signals is four micrometers. The two quadrature output signals are converted to eight-bit digital signals at a rate of 2.5 million times per second by analog-to-digital converters 103. The two eight-bit digital signals are supplied to lookup EPROM 104 where they are converted to ten-bit angle and six-bit magnitude digital signals for use by the subsequent digital signal processing system. The ten-bit angle signal divides the four micrometers between optical lines into 1024 segments of 3.9 nanometers each.

The sign bit of each converter is sent to a programmable logic device 105, e.g., Cypress Semiconductor CY7C344, which has been programmed to generate count and direction signals. These signals go to a second programmable logic device 106, e.g., Cypress Semiconductor CY7C344, which keeps track of how many lines have been crossed and in what direction, and which has been programmed to be a fourteen-bit up/down counter. Fourteen bits provides counts from −8,192 to +8,191 which covers from −32,768 to +32,764 micrometers and thus covers the entire slide movement in either direction. The fourteen-bit line count is sign-extended to 16 bits and sent to the digital signal processor (DSP).

Figure 13C:
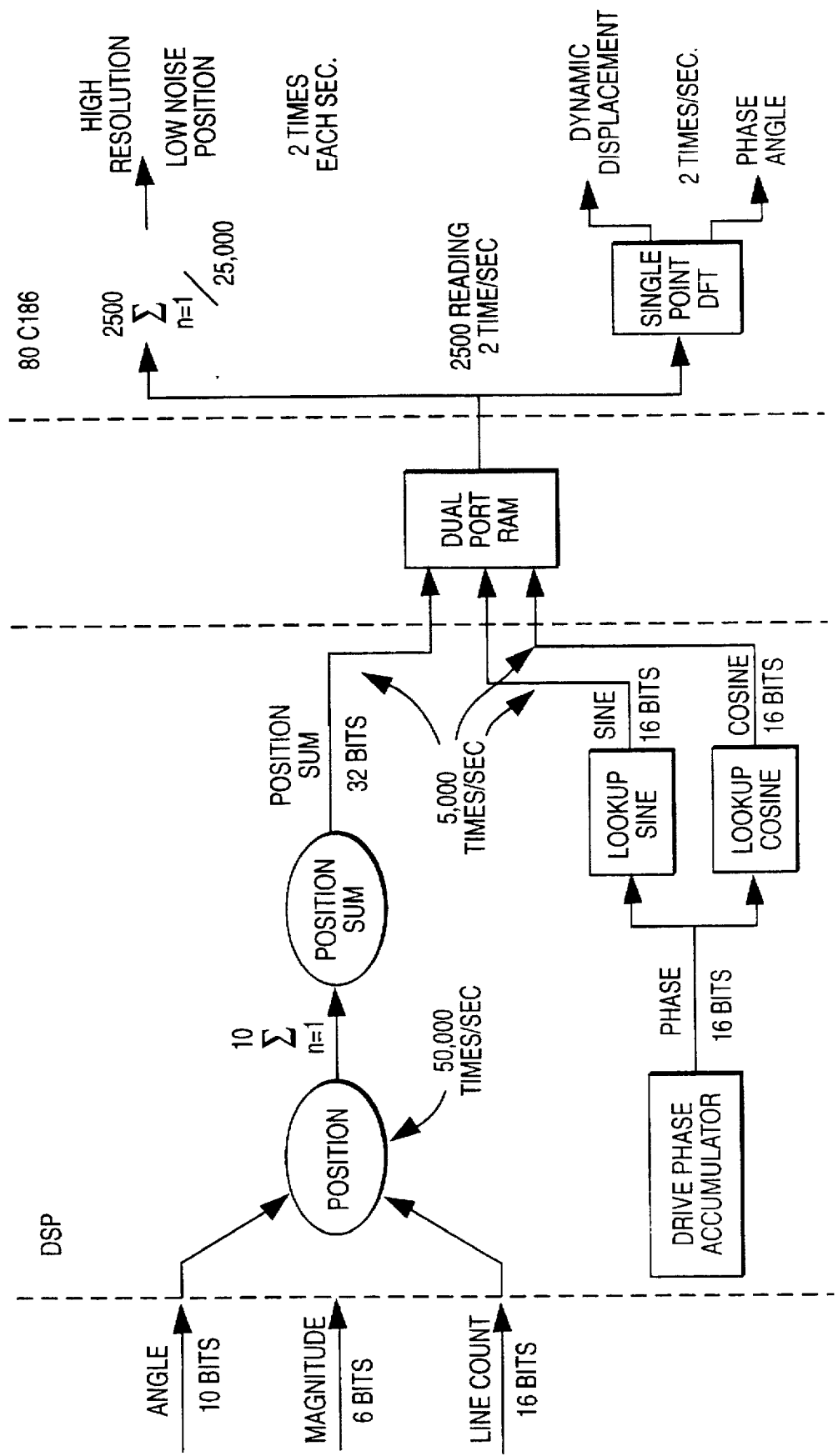
FIGS. 13C and 13D are schematic diagrams showing how the digital signals are processed within the digital signal processor and instrument microprocessor.

As shown in FIG. 13C, at step 107 the signal processor reads the position signal (ten-bit angle and fourteen-bit line count) 50,000 times each second. Each set of ten sequential values is processed by summing up the ten values in step 108, thus providing 5,000 thirty-two bit position values per second. The phase of the AC signal which is used to control the current to the linear motor driving drive rod 14 is accumulated in step 111, and converted to sixteen-bit sine and cosine values 5,000 times per second in step 112. The sine and cosine values representing the drive force, and the position sums representing the relative position of the slide (and the deformed segment of the sample) are placed into the circular queue of dual port RAM 109.

Figure 13D:
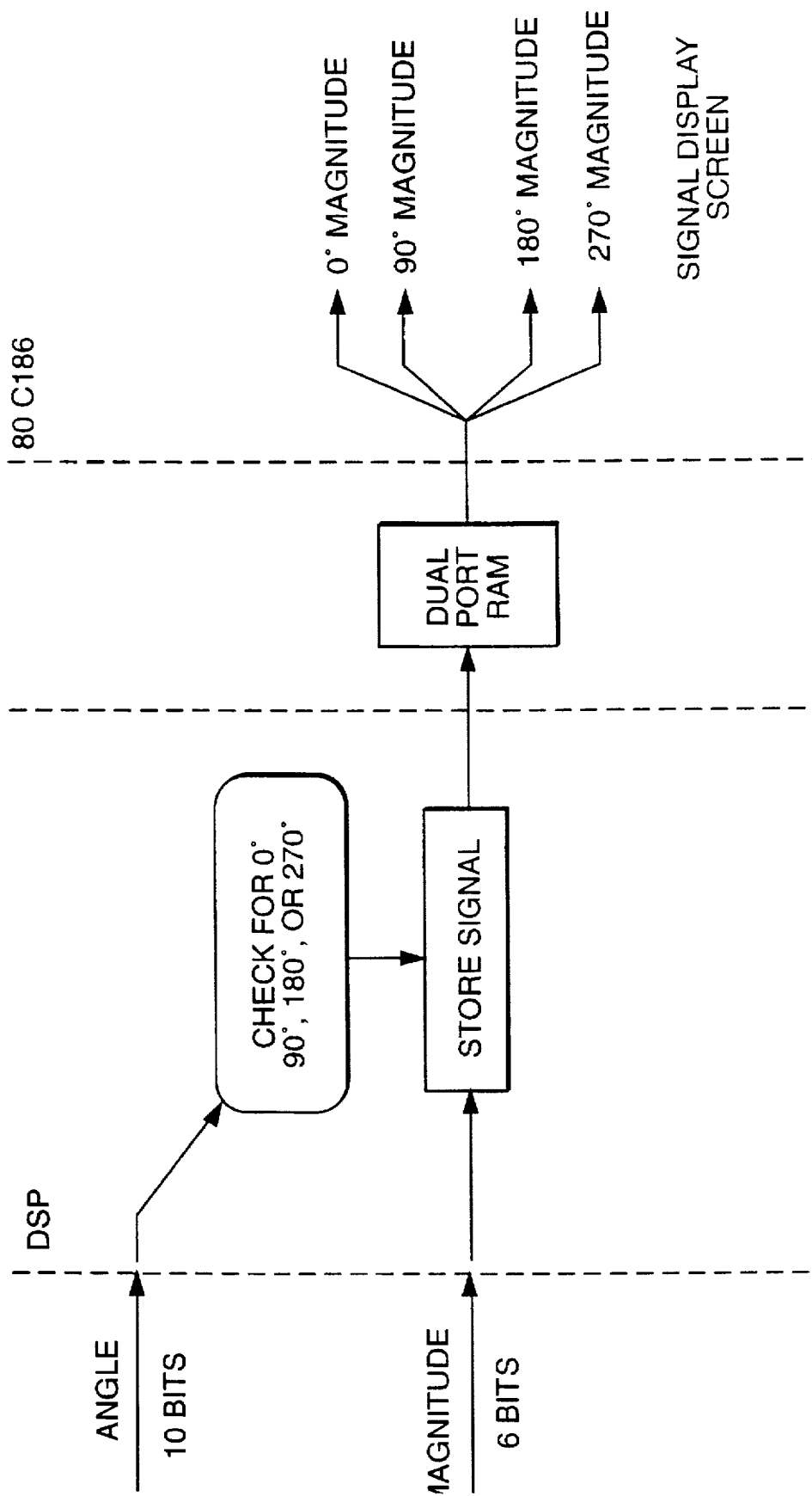

The six bit magnitude signal is used to make sure the two quadrature outputs of the photodetector system are well matched, such that the interpolation produces an accurate measure of the position of the slide. As shown in FIG. 13D, the six bit magnitude signal obtained from lookup table in EPROM 104 (ten bits of the sixteen bit EPROM is used for the angle data) and the angle signal are used to produce signals representing the magnitude of the output signals at 0°, 90°, 180° and 270°. The four magnitude signals are displayed on a display screen. If one of the four signals is smaller than the others, then interpolation values near the smaller signal's peaks will be spread out wider than 3.9 nanometers apart, and interpolation values near larger signals' peaks will be compressed closer than 3.9 nanometers.

This effect produces a sinusoidal error in the interpolated position reading that has a four micrometer period, and whose magnitude is related to the mismatch between the signals. The magnitude values near each of the two peaks of the two quadrature signals are displayed, and calibration potentiometers are used to match those values. This latter step could be automated.

Microprocessor 110 (e.g., an 80C186 microprocessor) reads the values in the queue of dual port RAM 109 (shown in FIG. 13C) and uses them to calculate data points twice each second. The data calculated includes an average position and a single point Fourier transform of that position. The Fourier transform results are the magnitude of sample oscillation and the phase relative to the drive signal.

Because 25,000 position readings are used to calculate each data point, there is a potential for signal noise reduction by the square root of 25,000, or about 158. Assuming that the noise or uncertainty in each position reading is about 40 nanometers, and that the noise is random from reading to reading, the resulting data file noise would be about one quarter of a nanometer. The noise in each position reading is somewhat correlated between position readings and thus the noise reduction is less, and the resulting noise is somewhat greater than one quarter of a nanometer.

The Fourier transform also processes 25,000 position readings to calculate the magnitude and phase of sample oscillation. This process is a little more complicated since it involves multiplying each 10 point average by a sine and a cosine value before summing the results and then finding the square root of the sum of the squares for the magnitude and the arc tangent of the ratio for the phase. However, since the sine and cosine values are from an ideal, noiseless drive signal, no noise is added to the position values and the noise reduction described above takes place.

The measured amplitude of oscillation of the sample and the phase of that oscillation relative to the oscillation of the drive force applied to the sample, along with the phase of the oscillating drive force applied to the sample, are used to calculate the storage modulus and the loss modulus of the sample.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A mechanical analyzer comprising:

(a) a frame;

(b) a linear permanent magnet motor comprising a fixed permanent magnet and a moving coil, wherein the fixed permanent magnet is attached to the frame of the mechanical analyzer;

(c) a slide having a first end and a second end, wherein the moving coil is rigidly attached to the second end of the slide, and wherein current applied to the coil causes the moving coil to apply a drive force to the slide;

(d) means for determining the magnitude of the drive force applied to the slide;

(e) an optical encoder comprising a diffraction grating attached to the slide, a light source attached to the frame, and a photodetector system attached to the frame, wherein a light beam produced by the light source is reflected by the diffraction grating back at the light photodetector system, such that the photodetector system detects two maxima and two minima per period of the diffraction grating as the slide moves vertically relative to the frame;

(f) a first plurality of bottom air bearings attached to the frame and a second plurality of top air bearings attached to the frame, wherein the bottom air bearings and the top air bearings cooperate to guide the slide within the air bearings such that it moves only in the vertical direction;

(g) a drive rod having a second end attached to the first end of the slide and a first end;

(h) a moving sample clamp assembly rigidly attached to the first end of the drive rod;

(i) a fixed sample clamp assembly rigidly attached to at least one vertical support, wherein said vertical support is attached to the frame at its second end;

(j) means for receiving electronic signals output by the photodetector system and combining the electronic signals to produce two quadrature output signals;

(k) means for converting the two quadrature output signals into digital angle and magnitude signals;

(l) means for receiving the digital angle signals and counting the maxima that have been detected, and means for keeping track of the direction of movement of the diffraction grating at each maximum;

(m) means for using the magnitude signals to match the magnitude of the two quadrature output signals to each other;

(n) means for interpolating the digital angle signals to calculate an interpolated position for the slide; and (o) means for calculating material properties of the sample based upon the interpolated positions of the slide as a function of the magnitude of the drive force applied to the slide.

2. The mechanical analyzer of claim 1, wherein the moving sample clamp assembly and the fixed sample clamp assembly are in a sample chamber, further comprising a sheet of thin reflective material spirally wound around the sample chamber, said sheet comprising a plurality of small protrusions maintaining the separation between successive layers of the spirally wound sheet.

3. The mechanical analyzer of claim 2, wherein the small protrusions are in a series of straight lines of protrusions, and the distance between consecutive straight lines of protrusions is random.

4. The mechanical analyzer of claim 2, further comprising a plurality of reflective disks forming a multilayer insulation system at the first end of the sample chamber, and a plurality of reflective disks forming a multilayer insulation system at the bottom of the sample chamber.

5. The mechanical analyzer of claim 2, wherein the sheet of thin reflective material is a stainless steel sheet.

6. The mechanical analyzer of claim 1, wherein the motor comprises an inner core and an air gap having a first end and a second end between the inner core and the permanent magnet, and wherein the air gap is tapered such that it is wider at the first end than at the second end.

7. The mechanical analyzer of claim 1, further comprising flat wires supplying electric current to the moving coil, wherein as the slide moves up and down the flat wires contact the slide in a frictionless rolling manner.

8. The mechanical analyzer of claim 1, wherein each of the first plurality of bottom air bearings and the second plurality of top air bearings is positioned against the surface of the slide by an adjusting screw.

9. The mechanical analyzer of claim 8, wherein each adjusting screw has a spherical end, and wherein the spherical end of each adjusting screw engages a conical cavity in the corresponding air bearing.

10. The mechanical analyzer of claim 1, further comprising a top resistance heating element mounted to the frame near the top of the frame, and a bottom resistance heating element mounted to the frame near the bottom of the frame, wherein the top and bottom heating elements are regulated to maintain a constant frame temperature.

11. A mechanical analyzer comprising:

(a) a frame;

(b) a linear permanent magnet motor comprising a fixed permanent magnet and a moving coil, wherein the fixed permanent magnet is attached to the frame of the mechanical analyzer;

(c) a slide having a first end and a second end, wherein the moving coil is rigidly attached to the second end of the slide, and wherein current applied to the coil causes the moving coil to apply a drive force to the slide;

(d) means for determining the magnitude of the drive force applied to the slide;

(e) an optical encoder comprising a diffraction grating attached to the slide, a light source attached to the frame, and a photodetector system attached to the frame, wherein a light beam produced by the light source is reflected by the diffraction grating back at the light photodetector system, such that the photodetector system detects two maxima and two minima per period of the diffraction grating as the slide is moved vertically relative to the frame;

(f) a first plurality of bottom air bearings and a second plurality of top air bearings, wherein the bottom air bearings and the top air bearings allow the slide to move in only the vertical direction;

(g) a drive rod having a second end attached to the first end of the slide and a first end;

(h) a moving sample clamp assembly rigidly attached to the first end of the drive rod;

(i) a fixed sample clamp assembly rigidly attached to at least one vertical support post, wherein said at least one vertical support post is attached to the frame at its second end;

(j) means for processing the signals output by the photodetector system to determine successive positions of the slide as the slide moves under the applied drive force with a resolution of at least four nanometers; and (k) means for calculating material properties of the sample based upon the determined positions of the slide as a function of the magnitude of the drive force applied to the slide.

12. The mechanical analyzer of claim 11, wherein the moving sample clamp assembly and the fixed sample clamp assembly are in a sample chamber, further comprising a thin metallic sheet spirally wound around the sample chamber, said metallic sheet comprising a plurality of small protrusions maintaining the separation between successive layers of the spirally wound sheet.

13. The mechanical analyzer of claim 11, wherein the motor comprises an inner core and an air gap having a first end and a second end between the inner core and the permanent magnet, and wherein the air gap is tapered such that it is wider at the first end than at the second end.

14. The mechanical analyzer of claim 11, further comprising flat wires supplying electric current to the moving coil, wherein as the slide moves up and down the flat wires contact the slide in a frictionless rolling manner.

15. The mechanical analyzer of claim 11, wherein each of the first plurality of bottom air bearings and the second plurality of top air bearings is positioned against the surface of the slide by an adjusting screw.

16. The mechanical analyzer of claim 11, further comprising a top resistance heating element mounted to the frame near the top of the frame, a bottom resistance heating element mounted to the frame near the bottom of the frame, and a thermal compensating plate attached to the top of the frame and closing the top of the frame, wherein the top and bottom heating elements are regulated to maintain a constant frame temperature.

17. The mechanical analyzer of claim 11, comprising a scanning reticle transparent phase grating attached to the frame between the light source and the diffraction grating, transmitting and modulating the light beam.

18. The mechanical analyzer of claim 11, wherein the moving sample clamp assembly and the fixed sample clamp assembly are in a sample chamber, further comprising a heating assembly comprising a plurality of vertical ceramic insulator rods circularly spaced around the sample chamber, rings at each end of the ceramic insulator rods connecting the rods together and forming a cylindrical cage, and a heating element helically wound around the ceramic insulator rods.

19. The mechanical analyzer of claim 11, wherein the moving sample clamp assembly and the fixed sample clamp assembly are in a sample chamber, further comprising an annular cooling jacket having an inner wall surrounding the sample chamber and an outer wall surrounding the inner wall and forming an annular cavity between the inner and outer walls.

20. The mechanical analyzer of claim 19, wherein the annular cavity is divided into a lower chamber and an upper chamber by a divider, said divider comprising a series of small holes evenly spaced around the divider.

21. A mechanical analyzer comprising:

(a) a frame;

(b) a linear permanent magnet motor comprising a fixed permanent magnet and a moving coil, wherein the fixed permanent magnet is attached to the frame of the mechanical analyzer;

(c) a slide having a first end and a second end, wherein the moving coil is rigidly attached to the second end of the slide, and wherein current applied to the coil causes the moving coil to apply a drive force to the slide;

(d) means for determining the magnitude of the drive force applied to the slide;

(e) an optical encoder comprising a diffraction grating attached to the slide, a light source attached to the frame, a grating reticle attached to the frame, and a photodetector system attached to the frame, wherein a light beam produced by the light source is modulated and reflected by the diffraction grating back at the photodetector system, and modulated and transmitted by the grating reticle, such that the photodetector system produces a modulated output signal as the slide is moved vertically relative to the frame;

(f) a first plurality of bottom air bearings and a second plurality of top air bearings, wherein the bottom air bearings and the top air bearings allow the slide to move in only the vertical direction;

(g) a drive rod having a second end attached to the first end of the slide and a first end;

(h) a moving sample clamp assembly rigidly attached to the first end of the drive rod;

(i) a fixed sample clamp assembly rigidly attached to a plurality of vertical support posts, wherein said vertical support posts are attached to the frame at their second ends;

(j) means for receiving the modulated output signal from the photodetector system and combining the electronic signals to produce two quadrature output signals;

(k) means for converting the two quadrature output signals into digital angle and digital magnitude signals;

(l) means for adjusting the amplitude of the two quadrature output signals such that they match each other;

(m) means for interpolating the digital angle signals to calculate an interpolated position for the slide; and (n) means for calculating material properties of the sample based upon the interpolated positions of the slide as a function of the magnitude of the drive force applied to the slide.

22. The mechanical analyzer of claim 21, comprising two analog-to-digital converters converting the quadrature output signals into two eight-bit digital signals.

23. The mechanical analyzer of claim 22, wherein the two eight-bit digital signals are converted to ten-bit angle and six-bit magnitude digital signals.

24. The mechanical analyzer of claim 23, wherein the sign bit of each analog-to-digital converter is supplied to a first programmable logic device which has been programmed to generate count and direction signals.

25. The mechanical analyzer of claim 24, wherein a second programmable logic device has been programmed to be a fourteen-bit up/down counter, and wherein the second programmable logic device receives the count and direction signals from the first programmable logic device and calculates a line count.

26. The mechanical analyzer of claim 25, comprising a signal processor which reads the ten-bit angle digital signal and the fourteen-bit line count digital signal to calculate a position signal at a first rate.

27. The mechanical analyzer of claim 26, wherein each set of ten consecutive position signals are summed, providing a position signal at a second rate which is one-tenth the rate of the first rate.

28. The mechanical analyzer of claim 27, wherein a phase signal derived from the means for determining the magnitude of the drive force applied to the slide is accumulated and converted to sixteen-bit sine and cosine values at the second rate.

29. The mechanical analyzer of claim 28, wherein the six-bit magnitude signal is displayed such that calibration potentiometers can be adjusted to adjust the relative magnitudes of the two quadrature output signals.

30. The mechanical analyzer of claim 28, wherein the moving sample clamp assembly and the fixed sample clamp assembly are in a sample chamber, further comprising a sheet of thin reflective material spirally wound around the sample chamber, said sheet comprising a plurality of small protrusions maintaining the separation between successive layers of the spirally wound sheet.

31. The mechanical analyzer of claim 30, wherein the sheet of thin reflective material is a sheet of thin stainless steel.

32. The mechanical analyzer of claim 28, wherein the motor comprises an inner core and an air gap having a first end and a second end between the inner core and the permanent magnet, and wherein the air gap is tapered such that it is wider at the first end than at the second end.

33. The mechanical analyzer of claim 28, further comprising flat wires supplying electric current to the moving coil, wherein as the slide moves up and down the flat wires contact the slide in a frictionless rolling manner.

34. The mechanical analyzer of claim 28, wherein each of the first plurality of bottom air bearings and the second plurality of top air bearings is positioned against the surface of the slide by an adjusting screw.

35. The mechanical analyzer of claim 28, further comprising a top resistance heating element mounted to the frame near the top of the frame, a bottom resistance heating element mounted to the frame near the bottom of the frame, and a thermal compensating plate attached to the top of the frame and closing the top of the frame, wherein the top and bottom heating elements are regulated to maintain a constant frame temperature.

36. The mechanical analyzer of claim 28, wherein the moving sample clamp assembly and the fixed sample clamp assembly are in a sample chamber, further comprising a heating assembly comprising a plurality of vertical ceramic insulator rods circularly spaced around the sample chamber, rings at each end of the ceramic insulator rods connecting the rods together and forming a cylindrical cage, and a heating element helically wound around the ceramic insulator rods.

37. The mechanical analyzer of claim 28, wherein the moving sample clamp assembly and the fixed sample clamp assembly are in a sample chamber, further comprising an annular cooling jacket having an inner wall surrounding the sample chamber and an outer wall surrounding the inner wall and forming an annular cavity between the inner and outer walls.

38. The mechanical analyzer of claim 37, wherein the annular cavity is divided into a lower chamber and an upper chamber by a divider, said divider comprising a series of small holes evenly spaced around the divider.

39. The mechanical analyzer of claim 28, further comprising a thin metallic sheet spirally wound around the sample chamber, said metallic sheet comprising a plurality of small protrusions maintaining a separation of 0.02 inches to 0.125 inches between successive layers of the spirally wound metallic sheet.

40. The mechanical analyzer of claim 39, wherein the metallic sheet is a stainless steel sheet with a thickness between 0.001 inches and 0.005 inches.

41. A mechanical analyzer comprising:
(a) a frame;
(b) a linear motor comprising a fixed magnet and a moving magnet, wherein the fixed magnet is attached to the frame of the mechanical analyzer, and wherein at least one of the fixed and moving magnets is an electromagnet having a coil;
(c) a slide having a first end and a second end, wherein the moving magnet is rigidly attached to the second end of the slide, and wherein current applied to the coil causes the coil to apply a drive force to the slide;
(d) means for controlling the magnitude of the drive force applied to the slide by controlling the current applied to the coil;
(e) means for determining the magnitude of the drive force applied to the slide;
(f) an optical encoder comprising a light source attached to the frame, an optical modulator attached to the slide, and a photodetector system attached to the frame, wherein a light beam produced by the light source is modulated by the optical modulator and directed to the photodetector system, such that the photodetector system produces a modulated output signal as the slide is moved relative to the frame;
(g) at least one air bearing, wherein the at least one air bearing constrains the slide such that it can slide in only one direction;
(h) a drive rod having a first end and a second end, wherein the second end of the drive rod is attached to the slide;
(i) a moving sample clamp assembly rigidly attached to the first end of the drive rod;
(j) a fixed sample clamp assembly rigidly attached to a support structure, wherein said support structure is attached to the frame;
(k) means for receiving the modulated output signal from the photodetector system and combining the electronic signals to produce output signals and for converting the output signals into digital angle and digital magnitude signals;
(l) means for interpolating the digital angle signals to calculate an interpolated position for the slide; and
(m) means for calculating material properties of the sample based upon the interpolated positions of the slide as a function of the magnitude of the drive force applied to the slide.

42. The mechanical analyzer of claim 41, wherein the fixed magnet is a permanent magnet and the moving magnet is an electromagnet.

43. The mechanical analyzer of claim 41, wherein the optical modulator is a diffraction grating.

44. The mechanical analyzer of claim 41, wherein the slide has a rectangular cross-section, and wherein the at least one air bearing comprises two sets of four air bearings.

45. The mechanical analyzer of claim 41, wherein the moving sample clamp assembly and the fixed sample clamp assembly are in a sample chamber, further comprising a thin metallic sheet spirally wound around the sample chamber, said metallic sheet comprising a plurality of small protrusions maintaining the separation between successive layers of the spirally wound sheet.

46. The mechanical analyzer of claim 41, wherein the fixed magnet is a permanent magnet, and wherein the motor comprises an inner core and an air gap having a first end and a second end between the inner core and the permanent magnet, and wherein the air gap is tapered such that it is wider at the first end than at the second end.

47. The mechanical analyzer of claim 41, further comprising flat wires supplying electric current to the moving coil, wherein as the slide moves up and down the flat wires contact the slide in a frictionless rolling manner.

48. The mechanical analyzer of claim 41, wherein the frame is mounted on elastomeric vibration isolation mounts.

49. The mechanical analyzer of claim 48, wherein natural frequencies of vibrations of the mechanical analyzer on the elastomeric isolation mounts are well below resonant frequencies of structures supporting the mechanical analyzer.

50. The mechanical analyzer of claim 41, wherein the moving sample clamp assembly and the fixed sample clamp assembly are in a sample chamber, further comprising a heating assembly comprising a plurality of vertical ceramic insulator rods circularly spaced around the sample chamber, rings at each end of the ceramic insulator rods connecting the rods together and forming a cylindrical cage, and a heating element helically wound around the ceramic insulator rods.

51. The mechanical analyzer of claim 41, wherein the moving sample clamp assembly and the fixed sample clamp assembly are in a sample chamber, further comprising an annular cooling jacket having an inner wall surrounding the sample chamber and an outer wall surrounding the inner wall and forming an annular cavity between the inner and outer walls.

52. The mechanical analyzer of claim 51, wherein the annular cavity is divided into a lower chamber and an upper chamber by a divider, said divider comprising a series of small holes evenly spaced around the divider.

53. The mechanical analyzer of claim 52, wherein the holes can be characterized by their total area, and wherein the total area of the holes in the divider is not greater than about 10% of the divider's total area.

* * * * *